(12) United States Patent
Wegerer et al.

(10) Patent No.: US 8,283,507 B2
(45) Date of Patent: Oct. 9, 2012

(54) WATER GAS SHIFT FOR ACETYLENE CONVERTER FEED CO CONTROL

(75) Inventors: David A. Wegerer, Lisle, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 200 days.

(21) Appl. No.: 12/917,805

(22) Filed: Nov. 2, 2010

(65) Prior Publication Data
US 2012/0108865 A1 May 3, 2012

(51) Int. Cl.
*C07C 5/08* (2006.01)

(52) U.S. Cl. ......... 585/254; 585/259; 585/833; 208/189

(58) Field of Classification Search .................. None
See application file for complete search history.

(56) References Cited

U.S. PATENT DOCUMENTS

| | | |
|---|---|---|
| 6,627,666 B1 | 9/2003 | Pedersen |
| 6,726,850 B1 | 4/2004 | Reyes |
| 7,009,085 B2 | 3/2006 | Cheung |
| 7,041,271 B2 | 5/2006 | Drnevich |
| 7,408,091 B2 | 8/2008 | Johnson |
| 2006/0178262 A1 | 8/2006 | Rokicki |
| 2008/0300437 A1 | 12/2008 | Johnson |
| 2009/0008292 A1 | 1/2009 | Keusenkothen |
| 2009/0170965 A1 | 7/2009 | Kibby |
| 2011/0144397 A1* | 6/2011 | van Egmond et al. ........ 585/256 |
| 2012/0107182 A1 | 5/2012 | Wegerer |

FOREIGN PATENT DOCUMENTS
EP    1710222 A2    11/2006

OTHER PUBLICATIONS

Huang, Selective Hydrogenation of Acetylene in the Presence of Ethylene on Zeolite-Supported Bimetallic Catalysts, Journal of Catalysis v. 246, n. 1 (2007) p. 40-51.
Park, Deuterium Tracer Study on the Effect of CO on the Selective Hydrogenation of Acetylene Over Pd/Al2O3, Industrial & Engineering Chemistry Research, v. 30, n. 8, p. 1693-1699.
Schbib, Kinetics of Front-End Acetylene Hydrogenation in Ethylene Production, Industrial & Engineering Chemistry Research, 1996, 35, p. 1496-1505.
Sexton, The Hydrogenation of CO and CO2 Over Polycrystalline Rhodium: Correlation of Surface Composition, Kinetics and Product Distributions, Journal of Catalysis 46, (1977), p. 167-189.
Trimm, The Effect of Carbon Monoxide on the Oligomerization of Acetylene in Hydrogen Over a Ni/SiO2 Catalyst, Journal of Molecular Catalysis A: Chemical, 307 (2009) p. 13-20.
Zhvanetskii, The Effect of Carbon Monoxide on the Hydrogenation of Acetylene (impurity) in Ethylene, Neftekhimiya (ISSN 0028-2421) v. 31, n. 3, p. 318-321, May-Jun. 1991, East View Publications, (English abstract).

* cited by examiner

*Primary Examiner* — Tam M Nguyen
(74) *Attorney, Agent, or Firm* — Arthur E Gooding

(57) ABSTRACT

A process and apparatus are presented for the removal of carbon monoxide from ethylene streams. The removal of carbon monoxide before selective hydrogenation protects the catalyst in the selective hydrogenation reactor. Carbon monoxide levels are controlled with the water gas shift process to convert the carbon monoxide to carbon dioxide, with the carbon dioxide removed in an acid gas removal process.

19 Claims, 2 Drawing Sheets

US 8,283,507 B2

WATER GAS SHIFT FOR ACETYLENE CONVERTER FEED CO CONTROL

FIELD OF THE INVENTION

The field of the invention is the production of ethylene. In particular, the invention pertains to the removal of carbon monoxide from an ethylene stream.

BACKGROUND OF THE INVENTION

Light olefins are important feed materials for the production of many chemicals, and products, such as polyethylene. The production of light olefins, and in particular ethylene, is through steam or catalytic cracking processes. The cracking processes take larger hydrocarbons, such as paraffins, and convert the larger hydrocarbons to smaller hydrocarbons products. The primary product is ethylene. However, there are numerous other chemicals produced in the process. Among the many byproducts are hydrogen, methane, acetylene, ethane. Also contaminants are generated in the process, such as CO, $CO_2$, and $H_2S$. To produce a high quality ethylene product, the contaminants and byproducts are removed to achieve a purity level of greater than 99.9% by volume of ethylene. In order to achieve this, the acid gases must be removed as well as the other by products.

In the process of purification, a portion of the ethylene is lost to the waste streams. Methods of reducing loss and increasing yields can have significant economic benefits.

SUMMARY OF THE INVENTION

Carbon monoxide is a problem contaminant for the selective hydrogenation process. A process for treating an ethylene stream having carbon monoxide is presented. The process includes passing a light olefin product stream comprising ethylene to an acid gas removal unit to create a de-acidified light olefin product stream. The de-acidified light olefin product stream is passed to a water gas shift reactor, where the gas is treated to remove CO, and create an effluent stream with a reduced CO concentration and an increased hydrogen concentration. The effluent stream is passed to a selective hydrogenation unit for the conversion of acetylene to ethylene, thereby creating an enriched product stream. The enriched product stream is passed to an ethylene recovery unit to generate an ethylene product stream.

In one embodiment, the process includes a second acid gas removal unit. The effluent stream from the water gas shift reactor has an increased carbon dioxide content. The effluent stream is passed to the second acid gas removal unit to create a de-acidified water gas shift effluent stream. The de-acidified effluent stream is then passed to a selective hydrogenation unit for the conversion of acetylene to ethylene, thereby creating an enriched product stream. The enriched product stream is passed to an ethylene recovery unit to generate an ethylene product stream.

Other objects, advantages and applications of the present invention will become apparent to those skilled in the art from the following detailed description and drawings.

DETAILED DESCRIPTION OF THE INVENTION

The production of ethylene includes catalytic and thermal cracking of hydrocarbon feedstocks. The cracking process generates a vapor stream comprising light olefins and other hydrocarbons. The vapor stream is passed to a compression system. The compressed stream is separated into a light vapor stream comprising ethylene and lighter components, and a heavier liquid stream comprising $C_3$ and heavier hydrocarbons. The light vapor stream is passed through a primary absorber to collect $C_3$ and higher HCs from the vapor phase. The primary absorber flow overhead (or vapor stream) is passed to a sponge absorber to remove residual heavy hydrocarbons, mostly $C_5$s. The sponge absorber uses a lean oil to absorb the residual heavier HCs, and the lean oil is either unstrapped light cycle oil or unstrapped heavy naphtha from the main fractionator in a refinery. The lean oil is cooled by exchange with the sponge absorber bottoms and then with either air or water coolers. The sponge oil is regenerated by returning it to the main fractionator to strip out the absorbed gases.

After the compression separation of $C_3$+ components form the cracking process stream an effluent rich in ethylene is left, but includes byproducts such as acetylene, ethane, hydrogen and methane, and contaminants such as carbon monoxide (CO), carbon dioxide ($CO_2$) and hydrogen sulfide ($H_2S$). Acetylene can be converted to ethylene through selective hydrogenation, to reduce the acetylene concentration to a level sufficiently low for a high purity ethylene product. The typical level of acetylene in polymer grade ethylene is less than 5 ppm by volume. The selective hydrogenation is adversely affected by the presence of carbon monoxide. Polymer grade ethylene is typically 99.9 vol. % or greater ethylene, with less than about 10 ppm acid gases and less than about 0.1 vol % methane and ethane.

The selective hydrogenation catalyst is adversely affected by too much CO, and the removal of CO obviates the need for special reactor designs to overcome relatively high CO concentrations. In some cases the CO concentration is too low, and CO is purposefully added to attenuate the selective hydrogenation catalyst activity. The control with a water gas shift reactor can allow maintenance of CO concentrations in acceptable ranges.

The present invention is a process for removing the carbon monoxide in the ethylene process stream to increase the performance of the selective hydrogenation of acetylene and therefore increase the yield of ethylene. The present invention also produces hydrogen for use in the selective hydrogenation of acetylene.

Figure 1:
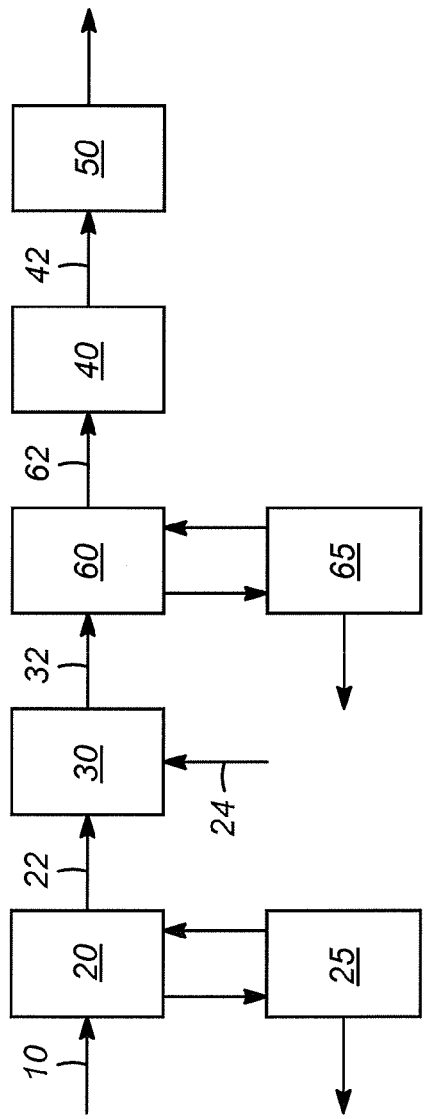
FIG. 1 is a process flow diagram of the invention.

The process of the present invention is as shown in FIG. 1. A light olefin product stream 10 is passed to an acid gas removal unit 20, to create a de-acidified light olefin product stream 22. The de-acidified olefin stream 22 is passed to a water gas shift reactor 30, where water is reacted with carbon monoxide to produce carbon dioxide and hydrogen, creating a treated stream 32 having a reduced CO concentration and an increased $H_2$ concentration. The treated stream 32 is passed to a selective hydrogenation unit 40 for the conversion of acetylene to ethylene, creating an enriched ethylene product stream 42. The enriched product stream 42 is passed to an ethylene recovery unit 50 to recover a purified ethylene product.

The process can further include passing water 24 to the water gas shift reactor 30 to ensure sufficient water for the equilibrium to consume the CO. The water gas shift reactor is operated at a temperature of at least 210° C., with a preferable temperature of the reactor between 230° C. and 260° C. In one embodiment, the process further includes passing the water gas shift reactor effluent stream 32 to a second acid gas removal unit 60, thereby creating a treated stream 62 with reduced $CO_2$ content. The second acid gas removal unit 60 removes $CO_2$ created by the water gas shift reactor 30. The flow in the water stream 24 to the water gas shift can be controlled to minimize the CO content in the effluent gas stream 32. The CO concentration in the effluent stream 32 can be monitored with a CO detector, with a feedback to control the amount of water admitted to the reactor in response to the CO detector.

The water gas shift reactor 30 is a catalytic reactor that contacts a gas having CO and water to form $CO_2$ and $H_2$. The catalyst in the reactor can be a metal oxide, a metal oxide on a support, or a mixture of metal and metal oxides. The preferred choices of metal oxides include iron oxide, chromic oxide, or mixtures of copper, zinc oxide, and alumina.

The enriched product stream 42 entering the ethylene recovery unit 50 is passed through a demethanizer, to remove methane and lighter gases from the product stream 42. The effluent from the demethanizer is passed to an ethylene-ethane splitter to separate the demethanized stream into an ethylene product stream and a bottoms stream comprising mostly ethane, but also including heavier components that have passed through the process.

The acid gas removal units comprise an amine treatment system for reducing the $CO_2$ and $H_2S$ concentrations to ppm levels and sub-ppm levels respectively. The acid gas removal units can also comprise other chemical or physical treatment systems for the removal of $CO_2$ and $H_2S$.

One embodiment of the invention is a system for reducing the CO content in the ethylene stream being passed to the selective hydrogenation reactor. The system comprises a first acid gas removal unit 20 having an inlet for admitting an ethylene rich gas stream and an outlet for passing the de-acidified ethylene stream to a water gas shift reactor 30. The ethylene rich gas stream is produced from a catalytic or steam cracking unit and heavier hydrocarbons having 3 or more carbons are separated in a compression separation system. The water gas shift reactor 30 has an inlet in fluid communication with the first acid gas removal unit 20 and an outlet for the water gas effluent stream having a reduced CO content and increased $H_2$ content. The water gas shift reactor 30 includes a CO sensor positioned in the effluent stream from the reactor 30, and provides control to a water supply to the reactor 30. A second acid gas removal unit 60 has an inlet in fluid communication with the reactor 30 effluent, and an outlet for the treated gas stream. A selective hydrogenation unit 40 has an inlet in fluid communication with the second acid gas removal unit 60 outlet, and an outlet for passing the selective hydrogenation effluent stream. An ethylene recovery unit 50 has an inlet in fluid communication with the selective hydrogenation unit 40 effluent.

The acid gas removal units 20, 60 include regenerators, where each acid gas removal unit comprises an absorber for contacting the ethylene rich stream with a solvent for absorbing the acid gases. The primary acid gases absorbed are $CO_2$ and $H_2S$. The absorbers include an inlet for admitting the ethylene gas and an outlet for passing the de-acidified ethylene gas, and an inlet for admitting a lean solvent, and an outlet for removing the solvent enriched with $CO_2$ and $H_2S$. The enriched solvent is passed to a regenerator for removing the acid gases, and regenerating the solvent. The regenerated, or lean, solvent is returned to the absorbers.

Figure 2:
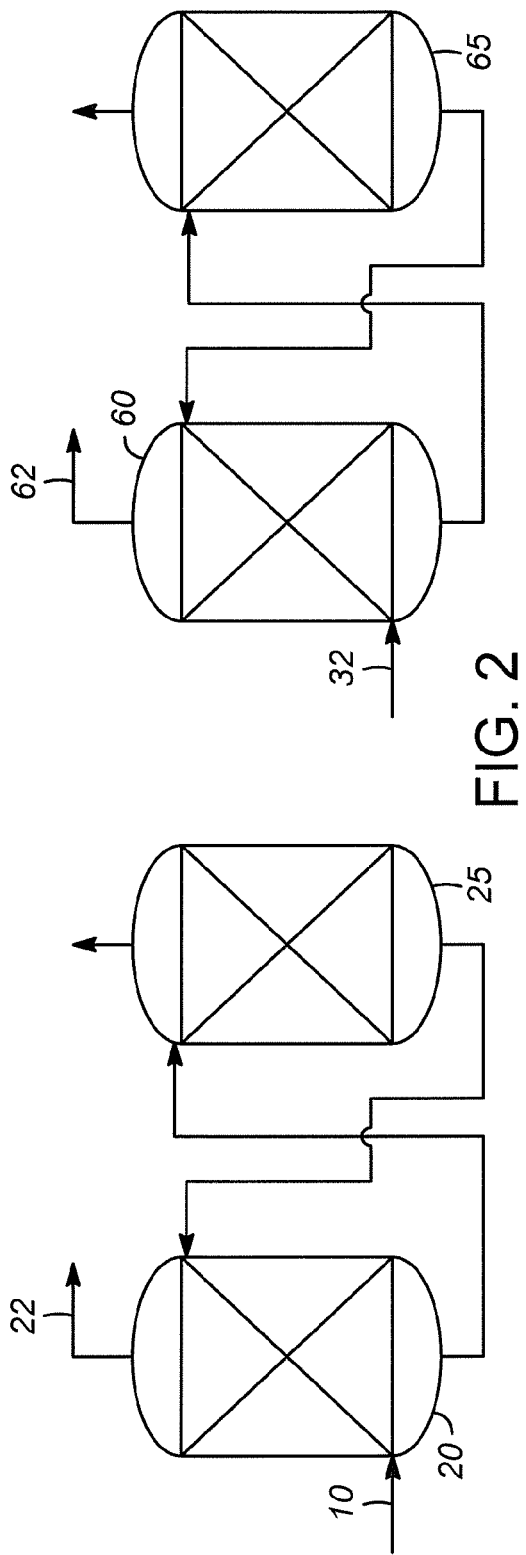
FIG. 2 is a diagram of one embodiment of the acid gas treating.

The acid gas removal units 20, 60 can have several configurations in the present invention. A first configuration is shown in FIG. 2 where the first acid gas removal unit 20 includes an absorber and a regenerator 25. The ethylene rich stream 10 containing $CO_2$ and $H_2S$ is contacted with a solvent for removing the acidic components of the gas. The rich solvent, containing the acidic components, is passed to the regenerator 25 and the acidic components are stripped from the solvent. The lean solvent is passed back to the absorber. The second acid gas removal unit 60 includes an absorber and a first regenerator 65. The effluent stream from the water gas shift reactor 32 is passed to the second acid gas unit 60 where the acidic components are removed from the water gas shift effluent. The primary component is $CO_2$ that is generated as a result of the water gas shift reaction, and is absorbed in a solvent passed to the absorber. The solvent is enriched with the acidic components and passed to a second regenerator 65 where the acidic components are stripped from the solvent, and the lean solvent is passed back to the absorber.

Figure 3:
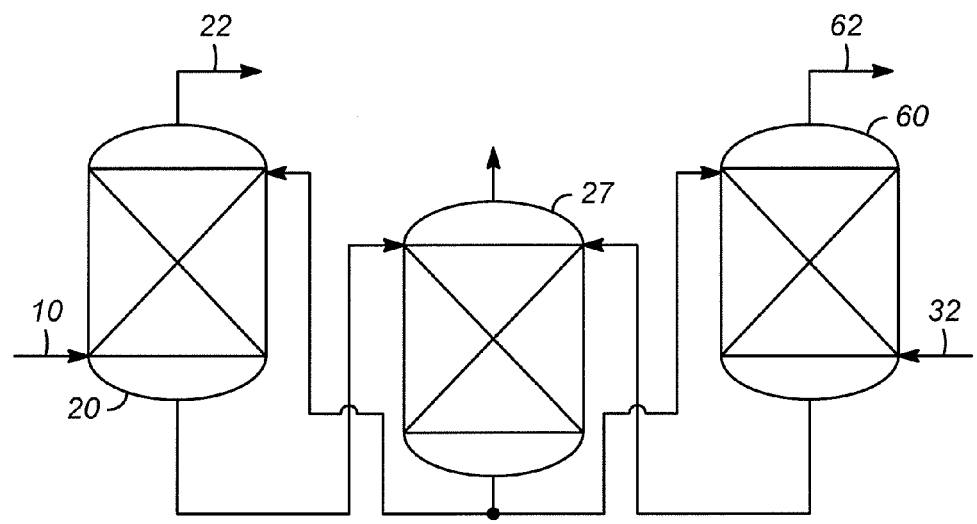
FIG. 3 is a diagram of a second embodiment of the acid gas treating.

A second configuration of the acid gas removal systems is shown in FIG. 3. The second configuration utilizes a single regenerator for both absorbers in the acid gas removal units 20, 60. The ethylene rich stream 10 containing $CO_2$ and $H_2S$ are stripped of the acid gases in the first absorber through contact with a solvent. The rich solvent is passed to the regenerator 27. The treated ethylene gas stream 22 after passing through the water gas shift reactor 30 generates an ethylene stream 32 with increased $CO_2$ content. The ethylene stream 32 is passed to the second absorber in the second acid gas removal unit 60 to generate a de-acidified stream 62, through contact with a solvent. The rich solvent is passed to the regenerator 27, and stripped of the acid gases, generating a lean solvent. The lean solvent stream is split and passed back to the first and second absorbers.

Figure 4:
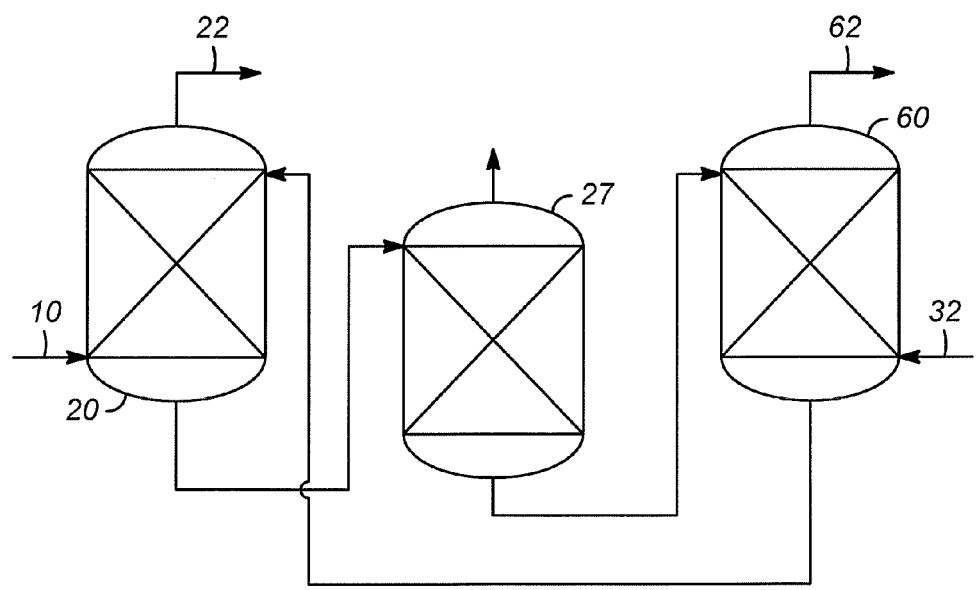
FIG. 4 is a diagram of a third embodiment of the acid gas treating.

A third configuration for the removal of acid gas is shown in FIG. 4. The third configuration utilizes a single regenerator 27 for both absorbers in the acid gas removal units 20, 60. The third configuration also takes advantage of the design where most of the acid gas is removed in the first acid gas removal unit 20. The ethylene rich stream 10 containing $CO_2$ and $H_2S$ are stripped of the acid gases in the first absorber through contact with a solvent. The rich solvent is passed to the regenerator 27 where the acid gases are stripped from the solvent. The lean solvent is passed to the second absorber where the solvent strips acid gas from the effluent stream 32 from the water gas shift reactor, creating a partially enriched solvent. The partially enriched solvent is passed to the first absorber in the first acid gas removal unit 20, where the partially enriched solvent strips more acid gas from the ethylene rich stream 10.

The process was simulated using a typical process stream from a fluidized catalytic cracking unit with the following results.

Example 1

The process of the present invention is shown with out water addition to the water gas shift reactor. The results are shown in Table 1. The water gas shift reaction conditions were a temperature of 232° C. (450° F.) and 1700 kPa (246.7 psia).

| Stream "A" | | | Stream "B" | |
|---|---|---|---|---|
| | Mole Fraction | Mole % | Mole Fraction | Mole % |
| $H_2O$ | 0.003893 | 0.3893 | 0.002525 | 0.2525 |
| Nitrogen | 0.063767 | 6.3767 | 0.063767 | 6.3767 |
| Hydrogen | 0.107293 | 10.7293 | 0.108660 | 10.8660 |
| CO | 0.002632 | 0.2632 | 0.001264 | 0.1264 |
| $CO_2$ | 0.000005 | 0.0005 | 0.001373 | 0.1373 |
| Methane | 0.250013 | 25.0013 | 0.250013 | 25.0013 |
| Acetylene | 0.000506 | 0.0506 | 0.000506 | 0.0506 |
| Ethylene | 0.488891 | 48.8891 | 0.488891 | 48.8891 |
| Ethane | 0.076927 | 7.6927 | 0.076927 | 7.6927 |
| Propylene | 0.006073 | 0.6073 | 0.006073 | 0.6073 |

Stream "A" is the feed stream 22 entering the water gas shift reactor, and stream "B" is the effluent stream 32 exiting the water gas shift reactor.

Example 2

The process was also run with water added to the water gas shift reactor. The reaction conditions of temperature and pressure were the same as in Example 1.

| Stream "A" | | | Stream "B" | |
|---|---|---|---|---|
| | Mole Fraction | Mole % | Mole Fraction | Mole % |
| H2O | 0.009843 | 0.9843 | 0.007828 | 0.7828 |
| Nitrogen | 0.063386 | 6.3386 | 0.063386 | 6.3386 |
| Hydrogen | 0.106652 | 10.6652 | 0.108667 | 10.8667 |
| CO | 0.002616 | 0.2616 | 0.000600 | 0.0600 |
| CO2 | 0.000005 | 0.0005 | 0.002021 | 0.2021 |
| Methane | 0.248519 | 24.8519 | 0.248519 | 24.8519 |
| Acetylene | 0.000503 | 0.0503 | 0.000503 | 0.0503 |
| Ethylene | 0.485971 | 48.5971 | 0.485971 | 48.5971 |
| Ethane | 0.076467 | 7.6467 | 0.076467 | 7.6467 |
| Propylene | 0.006037 | 0.6037 | 0.006037 | 0.6037 |

Although the water gas shift reaction reduced the CO content by more than 50%, there was still CO that could be removed. The use of additional water passed to the water gas shift reactor reduced the CO concentration by more than 75% of the CO in the gas stream 22 entering the water gas shift reactor.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for treating an ethylene product stream, comprising:
    passing the light olefin product stream to an acid gas removal unit to reduce the $H_2S$ and $CO_2$, thereby creating a de-acidified light olefin product stream;
    passing the de-acidified light olefin product stream to a water gas shift reactor, thereby generating a treated water gas shift effluent stream having a reduced CO concentration and an increased $H_2$ concentration;
    passing the effluent stream to a selective hydrogenation unit for the conversion of acetylene to ethylene, thereby creating an ethylene enriched product stream; and
    passing the enriched ethylene product stream to an ethylene recovery unit.

2. The process of claim 1 wherein the light olefin product stream is produced from a cracking process.

3. The process of claim 2 wherein the light olefin stream is produced from a steam cracker.

4. The process of claim 2 wherein the light olefin stream is produced from a catalytic cracker.

5. The process of claim 1 further comprising passing a water stream to the water gas shift reactor.

6. The process of claim 1 wherein the temperature in the water gas shift reactor is at least 210° C.

7. The process of claim 6 wherein the temperature in the water gas shift reactor is between 230° C. and 260° C.

8. The process of claim 1 further comprising passing the effluent from the water gas shift reactor to a second acid gas removal unit, thereby creating a treated stream with a reduced $CO_2$ content.

9. The process of claim 1 wherein the water gas shift reactor includes contacting the gas with a water gas shift catalyst.

10. The process of claim 9 wherein the water gas shift catalyst is selected from the group consisting of iron oxide, chromic oxide, mixtures of $Cu/ZnO/Al_2O_3$, and mixtures thereof.

11. The process of claim 1 wherein the ethylene recovery unit comprises:
    a demethanizer; and
    an ethylene-ethane splitter.

12. The process of claim 1 further comprising;
    testing the CO concentration in the effluent stream from the water gas shift reactor, and
    supplying water to the water gas shift reactor, wherein the water supply is controlled by the CO concentration in the effluent stream.

13. A process for treating an ethylene product stream, comprising:
    passing the light olefin product stream from a cracking unit to an acid gas removal unit to reduce the $H_2S$ and $CO_2$, thereby creating a sweetened light olefin product stream;
    passing the light olefin product stream to a water gas shift reactor, thereby generating a treated stream having a reduced CO concentration and an increased $H_2$ concentration;
    passing a water stream to the water gas shift reactor;
    passing the treated stream to a second acid gas removal unit, thereby creating a treated stream with a reduced $CO_2$ concentration;
    passing the treated stream with the reduced $CO_2$ concentration to a selective hydrogenation unit for the conversion of acetylene to ethylene, thereby creating an ethylene enriched product stream; and
    passing the enriched ethylene product stream to an ethylene recovery unit.

14. The process of claim 13 wherein the light olefin product stream is produced from a steam cracking process or a catalytic cracking process.

15. The process of claim 13 wherein the temperature in the water gas shift reactor is between 230° C. and 260° C.

16. The process of claim 13 wherein the water gas shift reactor includes contacting the gas with a water gas shift catalyst.

17. The process of claim 13 wherein the water gas shift catalyst is selected from the group consisting of iron oxide, chromic oxide, mixtures of $Cu/ZnO/Al_2O_3$, and mixtures thereof.

18. The process of claim 13 wherein the ethylene recovery unit comprises:
a demethanizer; and
an ethylene-ethane splitter.

19. The process of claim 13 further comprising:
testing the CO concentration in the effluent stream from the water gas shift reactor; and
supplying water to the water gas shift reactor, wherein the water supply is controlled by the CO concentration in the effluent stream.

* * * * *